United States Patent [19]

Opavsky et al.

[11] 4,306,092

[45] Dec. 15, 1981

[54] PROCESS FOR SEPARATING ACETALDEHYDE FROM MIXTURES WITH CHLOROFORM, METHYLENE CHLORIDE AND CHLOROFURAN

[75] Inventors: Werner Opavsky, Negros Oriental, Philippines; Josef Reisner, Cologne, Fed. Rep. of Germany

[73] Assignee: Wacker-Chemie GmbH, Munich, Fed. Rep. of Germany

[21] Appl. No.: 167,520

[22] Filed: Jul. 11, 1980

[30] Foreign Application Priority Data

Jul. 12, 1979 [DE] Fed. Rep. of Germany ....... 2928236

[51] Int. Cl.³ ..................... C07C 47/06; C07C 45/78
[52] U.S. Cl. ................................... 568/492; 568/449
[58] Field of Search ................... 568/491, 492, 449

[56] References Cited

U.S. PATENT DOCUMENTS

| | | | |
|---|---|---|---|
| 2,870,866 | 1/1959 | Baecklund | 568/492 |
| 3,154,588 | 10/1964 | Singleton | 568/492 |
| 3,616,271 | 10/1971 | Copelin et al. | 568/492 |

Primary Examiner—Werren B. Lone
Attorney, Agent, or Firm—Allison C. Collard; Thomas M. Galgano

[57] ABSTRACT

The invention provides a process by which acetaldehyde can be separated off from mixtures with chloroform, methylene chloride and chlorofuran. In this process, the aldehyde is separated off by adding water to separate the mixture into an aldehyde-containing phase and a phase comprising chloroform, methylene chloride and chlorofuran.

6 Claims, No Drawings

PROCESS FOR SEPARATING ACETALDEHYDE FROM MIXTURES WITH CHLOROFORM, METHYLENE CHLORIDE AND CHLOROFURAN

The present invention relates to a process for separating acetaldehyde from mixtures with chloroform, methylene chloride and chlorofuran.

The separation of organic, volatile, liquid compounds having different boiling points is carried out quite often by distillation in columns in both the laboratory and on an industrial scale, with a satisfactory degree of success. In this method, the compounds to be separated are heated, generally by indirect heat transfer by means of steam or liquid heat-transfer agents, until boiling and evaporation of the liquids occurs. Owing to the different vapor pressures of the various compounds present in the mixture, the percentage distribution of the components to be separated is different in the gas phase from that in the liquid phase. If the gas phase is separated from the liquid phase, which is in equilibrium with it, and is condensed and re-evaporated, concentration of the more volatile constituents, in turn, occurs in the gas phase. By repeating this process (rectification), separation of the various components is ultimately achieved, it being possible, in general, to draw off the desired substance as a pure substance at the top or at the bottom of the distillation column, while the remaining components are obtained at the respectively opposite end of the column. In the case of mixtures consisting of more than two components and having boiling points between the top and bottom temperatures of the column, such components have to be drawn off at side outlets of the column, frequently in admixture with portions of the other compounds to be separated.

Thus, for example, in the final distillation of acetaldehyde obtained from ethylene and air according to the two-stage Wacker process, the desired substance, acetaldehyde, is drawn off at the top of the column and the majority of the by-products is drawn off at the bottom of the column. In the above-mentioned manufacturing process, however, apart from the less volatile compounds, such as acetic acid and chlorinated aldehydes, moderately volatile compounds, such as, for example, chloroform, methylene chloride and 3-chlorofuran, are also produced. Although present only in small quantities, these moderately volatile compounds become concentrated in the upper half of the column during the final distillation because, owing to their boiling points, they are unable to leave the column at the bottom together with the other by-products. These compounds have to be drawn off at a side outlet of the column and they occur there together with acetaldehyde in a concentration of approximately only 2.5%. Since the acetaldehyde drawn off during the removal of these compounds, which constitutes proportionally more than 5% of the total product, must be recovered, the described side discharge is distilled again in another column. Whereas, in normal circumstances, in a distillation of this kind, the aldehyde would be drawn off at the top of the column and the chloroform at the bottom and consequently complete separation could occur, this is not possible in the present, special case.

The organic compounds containing chlorine and oxygen that are still present in the side discharge in addition to chloroform, methylene chloride and chlorofuran have such a strong tendency to become resinous that they would completely block any indirect heat-transfer agent in a very short time. To avoid this effect, the column is heated directly with steam which involves the disadvantage that, owing to the boiling point of water, the chloroform, methylene chloride and chlorofuran must again be drawn off not at the bottom, but at a side outlet. This side discharge consists of approximately 30% chloroform, methylene chloride, 3-chlorofuran and other by-products and approximately 70% acetaldehyde. Thus, in discarding this side discharge not only would some of the desired substance, acetaldehyde, be lost but also unnecessary costs would arise in burning or environmental pollution would be caused in the form of effluent contamination.

It is in this connection that the invention is of value in that it obviates the necessity for redistillation for the recovery of the desired substance on a reduced scale with the occurrence of the same problems, as described above, and makes possible practically loss-free recovery of the desired substance and yields the waste substances in a concentrated form and, therefore, in a form which can be put to use more economically.

The problem of the invention was to find a process which permits the desired substance, acetaldehyde, present in the above-mentioned side discharge to be economically recovered and which reduces contamination of the effluent from aldehyde plants manufacturing acetaldehyde from ethylene and air according to the two-stage process. This latter goal is important because both acetaldehyde and chloroform are detrimental to biological clarification plants not only as a result of the formation of fungus but also due to the inhibition of the biological degradation process.

The subject of the invention is a process for separating acetaldehyde from mixtures with chloroform, methylene chloride and chlorofuran, characterized in that, by adding water in an amount of from the same amount by weight to 15 times that amount, an aldehyde-containing aqueous phase and a phase consisting of chloroform, methylene chloride and chlorofuran are produced.

It has been found that, when working with mixtures consisting of acetaldehyde, chlorofuran, methylene chloride and chloroform, despite both the strong solubilizing action of acetaldehyde on chloroform/methylene chloride/chlorofuran in water and the ready solubility of acetaldehyde in chloroform/methylene chloride/chlorofuran, a distribution of chloroform/methylene chloride/chlorofuran and acetaldehyde in specific amounts of water takes place in such a manner that extensive separation of the acetaldehyde from the chloroform/methylene chloride/chlorofuran is achieved, in that the acetaldehyde becomes concentrated in the water, whereas the chloroform, methylene chloride and chlorofuran form a separate, water-insoluble phase.

It has been found that, on mixing water with acetaldehyde/chloroform/methylene chloride/chlorofuran mixtures which have a specific density of from 0.80 to 1.20, acetaldehyde goes extensively into solution in water, whereas, at the same time, the original chloroform/chlorofuran/methylene chloride/acetaldehyde mixtures becomes specifically heavier and does so in proportion as the specifically lighter acetaldehyde is removed from it. The resulting two phases of water-/acetaldehyde and water-insoluble chloroform/-chlorofuran/methylene chloride separate very readily on account of the difference in density.

The mixture may consist of from 40 to 90% by weight, preferably from 60 to 80% by weight, of acetaldehyde and, accordingly, from 10 to 60% by weight, preferably from 20 to 40% by weight, of the chlorine derivatives mentioned including impurities. The amount of chlorofuran may vary between 0.1 and 25% by weight, that of chloroform between 5 and 30% by weight, and that of methylene chloride between 0.5 and 5% by weight, based on the total mixture. The impurities constitute up to approximately 8% by weight. Examples of these are ethanol, ethyl acetate, chloracetaldehyde and crotonaldehyde. Water may also be present in the starting mixture.

Desalinated water or steam condensate can be used instead of water, and this is more advantageous in the redistillation of the aqueous aldehyde-containing phase. The temperature of the water should not exceed 40° C. The ratio of water to the liquid to be separated may be within the range of from 1:1 to 15:1 but is preferably within the range of from 2:1 to 5:1.

A further advantage of the invention is that mixtures of this kind that are to be separated by the process described above may also contain other compounds, such as, for example, crotonaldehyde or ethanol, crotonaldehyde remaining predominantly in the water-insoluble phase, while ethanol passes virtually quantitatively into the aqueous phase.

The process is preferably carried out by continuously introducing, into a separating vessel having a bottom outlet, water at a level above that of the bottom outlet but not higher than 20% of the active separating height of the separating vessel, introducing the mixture to be separated at a level above that of the water inlet, continuously or discontinuously drawing off the phase consisting of chloroform, methylene chloride and chlorofuran from the bottom outlet, and continuously drawing off the aldehyde-containing aqueous phase from the top.

The process for working up the side discharge of the side column in the two-stage process for the manufacture of acetaldehyde (see ULLMANN 1974, vol. 7, page 18, for a description of the two-stage process) is of particular relevance. In this process, by reacting ethylene with atmospheric oxygen in a liquid catalyst containing cupric chloride and palladium chloride, apart from the desired acetaldehyde, by-products such as chloroform, chlorofuran and methylene chloride are also produced, which become concentrated in the so-called side column during the purification of the acetaldehyde. These by-products are then removed from this column as a side discharge together with an unavoidable amount of approximately 70% acetaldehyde. Hitherto, this discharge had to be disposed of as waste liquor.

By means of the above-mentioned process, the acetaldehyde present in this side discharge can now be recovered in a yield of more than 95%, by returning the aqueous acetaldehyde-containing top product to the separating apparatus of acetaldehyde distillation, while the substances in the bottom discharge of the separating device, which would contaminate the effluent, can be burned in concentrated form.

In the following examples, the process of the present invention will be more fully described, and are given by way of illustration and not of limitation.

EXAMPLE 1

A glass column is used as the separating vessel. It consists of an empty 1 m retort section and five 1 m sections filled with Raschig rings of 12 mm diameter. The diameter of the column is 100 mm. At the lower end of the retort section is a bottom outlet, and the product supply nozzles are located between the individual sections. The top of the column is provided with an overflow.

A mixture consisting of 70% acetaldehyde, 18% chloroform, 7% 3-chlorofuran, 2% methylene chloride, 1% chloroacetaldehyde, 1% crotonaldehyde and 1% ethanol, as produced as the side discharge of the side column in the pure distillation of acetaldehyde according to the Wacker two-stage process, is continuously introduced above the third filled section, corresponding to 60% of the separating height of the column, at a rate of 10 kg/h. Cooled steam-condensate, at 15° C., entering at the upper end of the retort section, flows from below at a rate of 30 kg/h in a direction counter to the chloroform mixture.

The specifically heavier chloroform/chlorofuran/methylene chloride mixture, depleted of acetaldehyde, forming droplets in the retort is continuously drawn off. The steam-condensate, enriched with acetaldehyde, flows off continuously at the top of the column via the overflow.

98% of the acetaldehyde supplied to the column remains in the aqueous phase. 2% is found in the chloroform phase. 17% of the chloroform and 15% of the chlorofuran introduced are found in the aqueous phase, and 83% and 85%, respectively, remain as a heavy phase in the retort. The chloracetaldehyde is distributed between the two phases, 50% being present in each phase. 90% of the methylene chloride remains in the heavier chloroform phase.

EXAMPLE 2

The arrangement of the apparatus is the same as in Example 1. The chloroform/acetaldehyde mixture, however, is fed into the column at 80% of the column separating height corresponding to 4 m above the retort. This corresponds to an increase in the height of the lower separating column of 33%. Result:

The residual content of acetaldehyde in the chloroform phase falls, by approximately 50%, to 1% of the amount of acetaldehyde originally introduced.

EXAMPLE 3

A mixture consisting of 78% acetaldehyde, 8.5% chloroform, 0.25% chlorofuran, 2% methylene chloride, 0.25% crotonaldehyde, 0.45% ethanol and 10.55% water is introduced into an apparatus, which is the same as that described in Example 1 except that it is filled with 20 mm Raschig rings, at a level of 60% of the separating height above the retort, at a rate of 12 kg/h, in counter-current with 6.7 times the amount of completely desalinated water.

The aqueous phase continuously drawn off at the top of the column contains 99.9% of the acetaldehyde supplied to the column and more than 95% of the ethanol. The water-insoluble bottom phase contains 84% of the chloroform, more than 95% of the chlorofuran, more than 95% of the methylene chloride and more than 95% of the crotonaldehyde.

EXAMPLE 4

A mixture consisting of 74% acetaldehyde, 15% chloroform, 0.6% chlorofuran, 9.4% water and 1% methylene chloride is introduced into a glass column, which is the same as that described in Example 3, at a rate of 16 kg/h, at a level of 60% of the separating height. The ratio of of the inflowing mixture to water is 1:3. The aqueous phase continuously drawn off at the top of the column contains 99.8% of the acetaldehyde and 10% of the chloroform. The water-insoluble phase contains 90% of the chloroform, 94% of the chlorofuran, 90% of the methylene chloride and 0.2% of the acetaldehyde.

EXAMPLE 5

The arrangement of the apparatus is the same as in Example 1. The diameter of the Raschig rings is 20 mm. The ratio of chloroform/acetaldehyde to water is 1:2, and introduction into the column takes place 3 m above the retort section.

Results of Example 5
(Data in % by weight)

| Starting material | Inflow into column Kg | conc. % | $CHCl_3$—Phase Kg | conc. % | aqueous phase Kg | conc. % | % of inflow |
|---|---|---|---|---|---|---|---|
| Acetaldehyde | 6.45 | 43 | 0.11 | 1.55 | 6.34 | 16.72 | 98.2 |
| $CHCl_3$ | 3.75 | 25 | 3.40 | 48.02 | 0.35 | 0.9 | 7.3 |
| 3-Cl—furan | 3.45 | 23 | 3.10 | 43.78 | 0.35 | 0.9 | 10.0 |
| $CH_2Cl_2$ | 0.3 | 2 | 0.14 | 1.97 | 0.16 | 0.4 | 53 |
| Crotonaldehyde | 0.3 | 2 | 0.14 | 1.97 | 0.16 | 0.4 | 53 |
| Ethanol | 0.15 | 1 | 0.07 | 0.99 | 0.08 | 0.2 | 53 |
| Ethyl acetate | 0.15 | 1 | 0.07 | 0.99 | 0.08 | 0.2 | 33 |
| Chloroacetaldehyde | 0.075 | 0.5 | 0.04 | 0.56 | 0.035 | 0.1 | 47 |
| Water | 0.375 | 2.5 | 0.01 | 0.14 | 0.365 | remainder | |
| | 15 | 100.0 | 7.08 | 100.0 | 7.920 | | |

98.2% of the ACH is in the aqueous phase
92.7% of the $CHCl_3$ and 90% of the Cl—furan are in the heavier phase Thus, while only several examples of the present invention have been described, it will be obvious that many changes and modifications can be made in carrying out the present invention without departing from the spirit and scope thereof.

What is claimed is:

1. In a process for separating acetaldehyde from mixtures with chloroform, methylene chloride and chlorofuran, wherein the mixture to be separated is the side discharge of the side column obtained from the production of acetaldehyde from ethylene and air according to the two-stage process, the improvement comprising the steps of: adding to said mixture water in an amount of from the same amount by weight to 15 times that amount, calculated on the amount of said mixture, by continuously introducing the water into a separating vessel having a bottom outlet, at a level above that of the bottom outlet but not higher than 20% of the active separating height of the separating vessel, and by introducing the mixture to be separated at a level above that of the water inlet, thereby producing an acetaldehyde-containing aqueous phase and a phase containing chloroform, methylene chloride and chlorofuran;

drawing off the phase containing chloroform, methylene chloride and chlorofuran from the bottom outlet; and continuously drawing off the acetaldehyde-containing aqueous phase from the top.

2. The process according to claim 1, wherein said phase containing chloroform, methylene chloride and chlorofuran is drawn off continuously.

3. The process according to claim 1, wherein said phase containing chloroform, methylene chloride and chlorofuran is drawn off discontinuously.

4. The process according to claim 1, wherein the temperature of the water introduced does not exceed 40° C.

5. The process according to claim 1, wherein the mixture to be separated contains 40–90% by weight of acetaldehyde, calculated on the total amount of the mixture.

6. The process according to claim 1, additionally including the step of effecting the redistillation of the aqueous acetaldehyde-containing phase.

* * * * *